(12) United States Patent
Plishka et al.

(10) Patent No.: US 7,736,336 B2
(45) Date of Patent: Jun. 15, 2010

(54) PARACENTESIS DEVICE HAVING MULTIPLE DETACHABLE COMPONENTS

(75) Inventors: Michael Plishka, Northbrook, IL (US); Jeffrey Schmitt, Waukegan, IL (US); Gregory Groenke, Gurnee, IL (US)

(73) Assignee: Allegiance Corporation, McGaw Park, IL (US)

( * ) Notice: Subject to any disclaimer, the term of this patent is extended or adjusted under 35 U.S.C. 154(b) by 2708 days.

(21) Appl. No.: 09/952,781

(22) Filed: Sep. 13, 2001

(65) Prior Publication Data

US 2004/0049157 A1    Mar. 11, 2004

(51) Int. Cl.
*A61M 5/178* (2006.01)

(52) U.S. Cl. ...................................................... 604/158

(58) Field of Classification Search .............. 604/93.01, 604/164.01–164.02, 164.07–164.08, 165.01–165.02, 604/165.04, 167.01–167.06, 170.03, 158–163
See application file for complete search history.

(56) References Cited

U.S. PATENT DOCUMENTS

| | | | | |
|---|---|---|---|---|
| 3,856,009 A | * | 12/1974 | Winnie | 604/170.03 |
| 4,799,930 A | | 1/1989 | Knoch et al. | 623/2 |
| 4,917,668 A | | 4/1990 | Haindl | 604/167 |
| 4,968,308 A | | 11/1990 | Herlitze et al. | 604/280 |
| 5,078,688 A | | 1/1992 | Lobodzinski et al. | 604/164 |
| 5,078,689 A | | 1/1992 | Keller | 604/167 |
| 5,098,388 A | | 3/1992 | Kulkashi et al. | 604/158 |
| 5,147,333 A | | 9/1992 | Raines | 604/249 |
| 5,300,046 A | * | 4/1994 | Scarfone et al. | 604/264 |
| 5,322,518 A | | 6/1994 | Schneider et al. | 604/247 |
| 5,334,159 A | * | 8/1994 | Turkel | 604/158 |
| 5,342,326 A | | 8/1994 | Peppel et al. | 604/284 |
| 5,472,435 A | * | 12/1995 | Sutton | 604/540 |
| 5,562,611 A | | 10/1996 | Transue | 604/26 |
| 5,613,663 A | | 3/1997 | Schmidt et al. | 251/149.2 |
| 5,630,802 A | | 5/1997 | Moellmann et al. | 604/164 |
| 5,637,096 A | | 6/1997 | Yoon | 604/158 |
| 5,637,098 A | | 6/1997 | Bierman | 604/180 |
| 5,669,883 A | | 9/1997 | Scarfone et al. | 604/167 |
| 5,725,506 A | * | 3/1998 | Freeman et al. | 604/167.01 |
| 5,743,883 A | | 4/1998 | Visconti | 604/169 |
| 5,895,410 A | | 4/1999 | Forber et al. | 606/200 |
| 5,984,944 A | | 11/1999 | Forber | 606/191 |
| 5,997,486 A | | 12/1999 | Burek et al. | 600/573 |
| 6,217,556 B1 | | 4/2001 | Ellingson et al. | 604/167.01 |
| 6,811,545 B2 | * | 11/2004 | Vaillancourt | 604/158 |

* cited by examiner

*Primary Examiner*—Nicholas D Lucchesi
*Assistant Examiner*—Laura A Bouchelle
(74) *Attorney, Agent, or Firm*—Brinks Hofer Gilson & Lione

(57) ABSTRACT

The invention described herein relates to an improved device for paracentesis procedures, such as thoracentesis. The device comprises a cannula assembly, valve assembly, and catheter assembly, wherein the cannula assembly is removably attached to the valve assembly, and the valve assembly is removably attached to the catheter assembly. The device can comprise an externally viewable indicator revealing the relative positions of the cannula assembly components. The device can further comprise a locking mechanism which controls the movement between cannula assembly components and is activated and deactivated by the coupling of the cannula assembly to the valve assembly. The device improves the precision and safety of its handling, and offers the practitioner several aspiration alternatives while maintaining separation of the internal and external patient environments.

3 Claims, 11 Drawing Sheets

PARACENTESIS DEVICE HAVING MULTIPLE DETACHABLE COMPONENTS

FIELD OF THE INVENTION

The invention relates to the field of invasive medical devices. More particularly, the invention pertains to an improved paracentetic device useful in thoracentesis procedures, for example.

BACKGROUND OF THE INVENTION

Paracentesis is a medical procedure involving the insertion of a device into a body cavity and withdrawal of fluid therefrom. These procedures can be performed for general removal of fluid from the body cavity, or for analytical and diagnostic purposes. Thoracentesis is a paracentetic procedure involving access into the pleural cavity and removal of fluid therefrom without permitting the entry of air or backflow of fluids. The thoracentesis procedure, such as that used to treat pleural effusion, usually involves the use of a tube or catheter inserted through the chest wall and into the pleural cavity to withdraw fluid therefrom. Body fluids such as effluate and blood, as well as air, can be removed from the cavity by application of negative pressure or suction from outside the patient's body. One critical aspect to the procedure is the continual maintenance of negative pressure in the pleural cavity throughout the duration of the procedure. It is therefore, undesirable for commingling of the pleural environment and the external environment to occur, which can result in pneumothorax. Another critical aspect to the thoracentesis procedure is the avoidance of puncturing the lung tissue, which can permit the inflow of air in the lung into the pleural cavity.

A variety of device components have been developed to improve invasive devices and procedures. Puncture-resistant Veress needle assemblies are known in the art. Scarfone et al., U.S. Pat. No. 5,669,883 discloses, a Veress needle and cannula assembly where an inner and outer cannula are inserted within the catheter. Such devices, however, offer a limited extent of procedural alternatives.

There exists a need in the medical device field for an improved paracentesis device containing features which facilitate the use of the device by the practitioner and at the same time can maintain a closed environment throughout the procedure. There is also a need in the medical device field for improved paracentesis devices which afford the user alternative procedural options and flexibility of usage.

SUMMARY OF THE INVENTION

The invention provides for an improved paracentesis device comprising a cannula assembly, valve assembly, and catheter assembly. The device contains structural and functional features enhancing the accuracy and safety of the device, as well as offering procedural flexibility in aspiration procedures. The separation of the patient's internal environment and external environment can be maintained throughout the procedure with the device of the invention. The device is particularly useful in thoracentesis procedures. It has been discovered that a paracentesis device can be constructed so as to contain a plurality of removably attachable components as well as additional features which enhance the performance of the procedure, all collectively in compliance with the requirements for aspiration and paracentesis.

The invention provides a device for use in paracentesis comprising:

a) a cannula assembly comprising an inner cannula having an internal lumen and at least one lateral opening located proximal to its distal end, an outer cannula adapted to accommodate said inner cannula within, and cannula assembly housing, said inner cannula being movable relative to said outer cannula;

b) a valve assembly comprising a valve housing, interior chamber, reinsertible valve positioned within said chamber, and a lateral access port, said valve assembly adapted to removably attach to said cannula assembly and to accommodate a portion of said cannula assembly when placed within; and c) a catheter assembly comprising a flexible catheter having an internal lumen and at least one opening, said catheter assembly adapted to removably attach to said valve assembly and to accommodate the distal portion of said cannula assembly when placed within.

In one embodiment the cannula assembly of the device further comprises an externally viewable indicator revealing the position of the inner cannula relative to the outer cannula. In another embodiment, the device further comprises a locking mechanism controlled by the coupling of the cannula assembly to the valve assembly thereby permitting or restricting the movement of the inner cannula within the outer cannula. In yet another embodiment, the device comprises a flexible catheter having a pre-determined resting state configuration other than a substantially linear configuration, such as a coiled configuration.

DETAILED DESCRIPTION OF THE INVENTION

The term "paracentesis" refers to any invasive medical procedure which involves the removal or withdrawal of fluid from a body cavity. The term "thoracentesis" refers to a paracentetic procedure of the pleural cavity.

The term "aspiration device" as used herein is used to generally describe any device conventionally used in the medical field to withdraw fluid or air in a medical procedure. The term is intended to include syringes, bulbs, vacuum devices, and the like.

Figure 1:
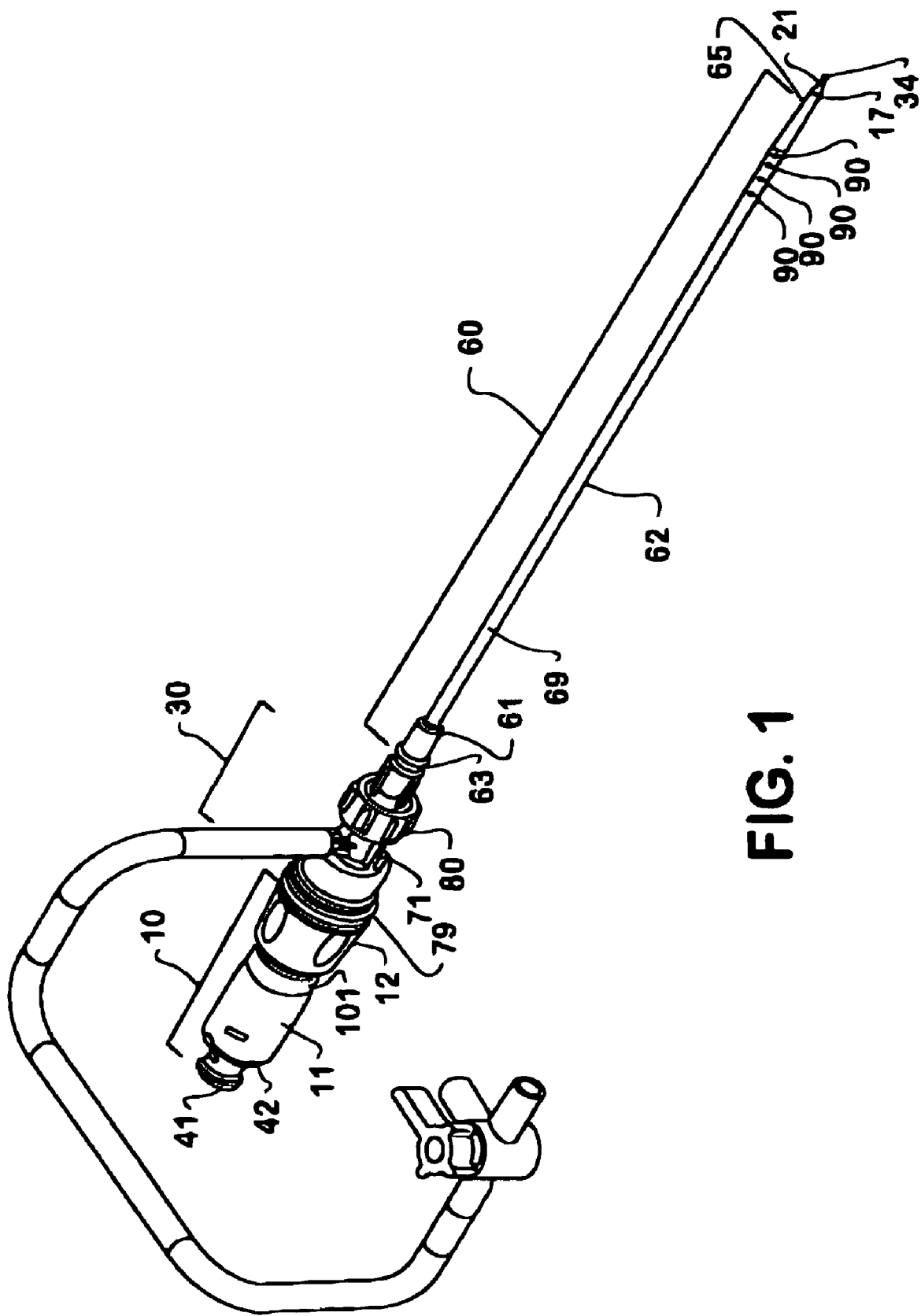
FIG. 1 is an overall perspective view of assembled device according to one embodiment of the invention showing additional attachments to the lateral access port.

Referring to FIG. 1, the device of the invention generally comprises a cannula assembly 10, valve assembly 30, and catheter assembly 60 whereby each of these components is removably attached to one another. The catheter assembly 60 is removably attached to the valve assembly 30, and the valve assembly 30 is removably attached to the cannula assembly 10. The valve assembly 30, therefore, is positioned between the distal portion 12 of the cannula assembly housing 11 and the proximal portion 61 of the catheter assembly 60, while the distal portion 13 of the cannula assembly 10 runs through the interior of the valve assembly 30 and catheter assembly 60 when the device is in assembled condition. The distal components of the assembled device, i.e., the catheter 62, inner cannula 15 and outer cannula 14 both residing within the catheter 62, are adapted for insertion and positioning within the body cavity in accordance with typical paracentesis procedures.

Figure 3:
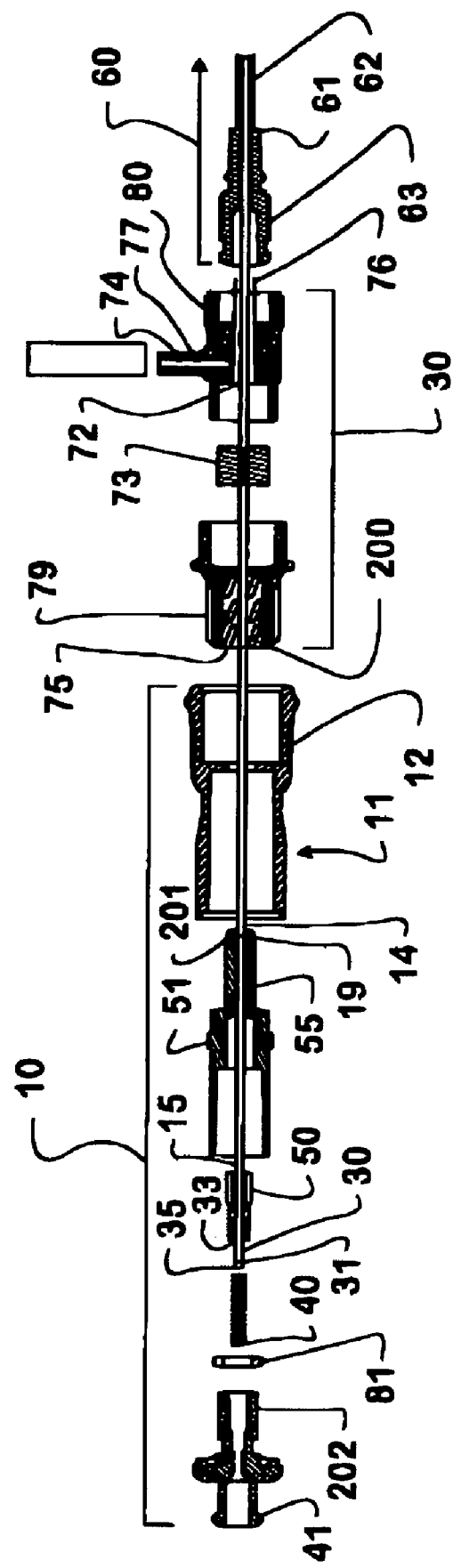
FIG. 3 is an exploded view in cross-section of a device showing individual components according to one embodiment of the invention.
Figure 4:
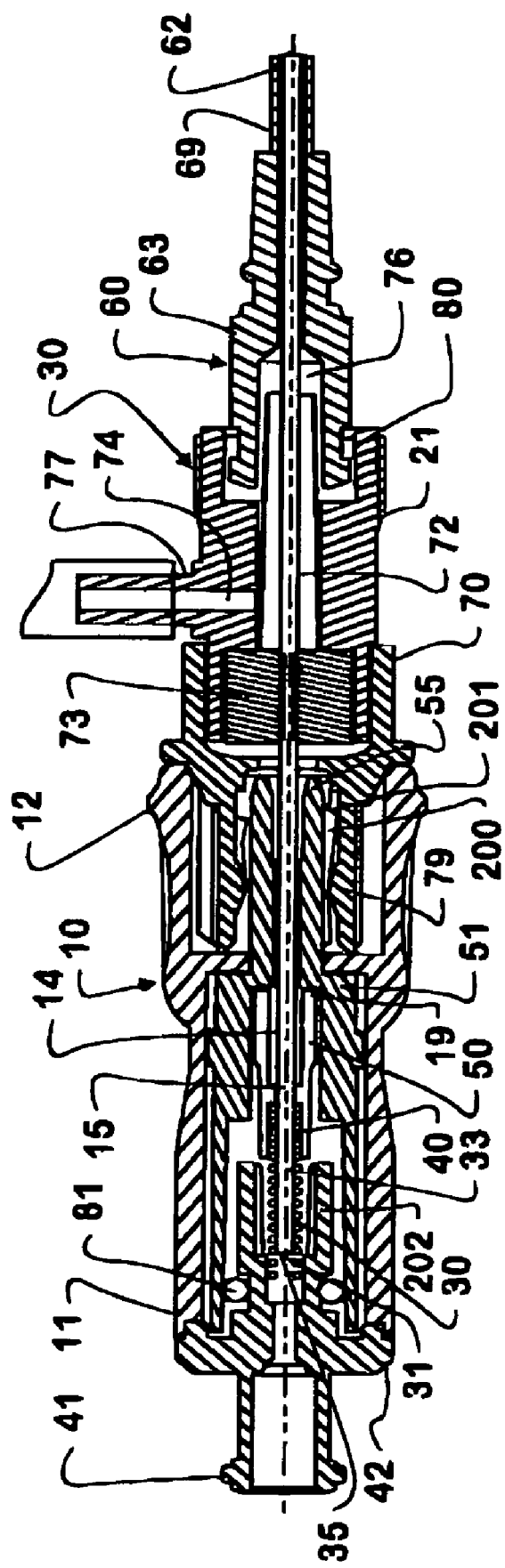
FIG. 4 is an interior cross-sectional side view of the proximal portion of the device showing internal assembly of components according to one embodiment of the invention.
Figure 5:
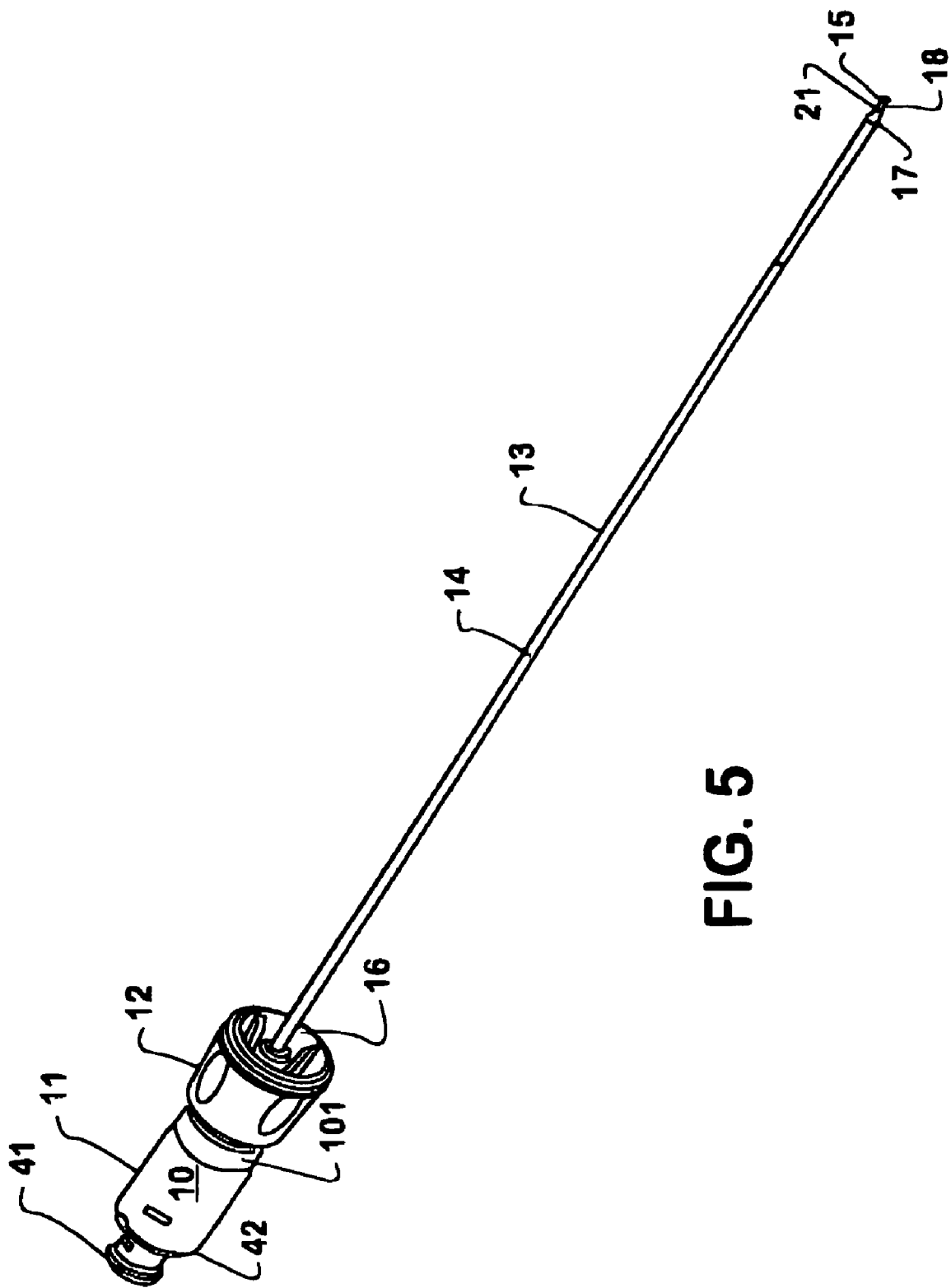
FIG. 5 is an overall perspective view of the cannula assembly portion according to one embodiment of the invention.
Figure 11:
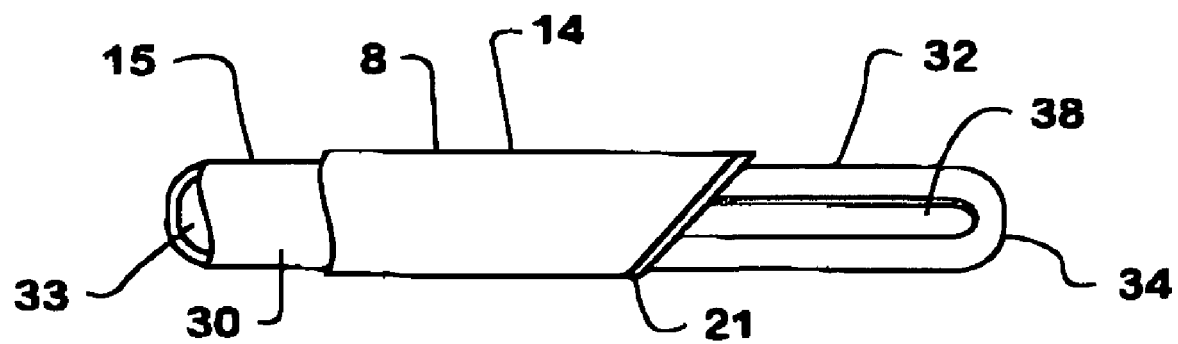
FIG. 11 is an enlarged side view of the distal end of the inner cannula extended beyond the distal end of the outer cannula superimposed thereon according to one embodiment of the invention.

Referring to FIG. 5, the cannula assembly 10 comprises an inner cannula 15, an outer cannula 14 adapted to accommodate the inner cannula, and cannula assembly housing 11. The inner cannula 15 and outer cannula 14 are arranged to form a Veress-type needle structure wherein the inner cannula 15 moves relative to the outer cannula 14. The outer cannula 14 comprises a longitudinal body 8 having proximal and distal ends (16 and 17 respectively) and an internal lumen running longitudinally therethrough, and comprises a distal opening 18 and a proximal opening 19. The outer cannula 14 is adapted to accommodate the inner cannula 15 when the inner cannula 15 is inserted within. The proximal portion 16 of the outer cannula 14 is affixed to the outer cannula hub 51 contained within the cannula assembly housing 11 as depicted in FIGS. 3 and 4. The distal tip 21 of the outer cannula 14 can comprise a sharp tapered cutting edge as illustrated in FIG. 11.

The inner cannula 15 is positioned within and is movable relative to the outer cannula 14. Thus, the inner diameter of the outer cannula 14 is slightly larger than the outer diameter of the inner cannula 15. The inner cannula 15 comprises a longitudinal hollow body 30 having a proximal end 31 and distal end 32 and an internal lumen 33 running therethrough. As shown in FIG. 11, the distal tip 34 of the inner cannula 15 is blunt, preferably smoothed and rounded. The blunt distal tip 34 of the inner cannula 15 reduces the likelihood of unintentional puncture of objects and surfaces coming into contact therewith, such as internal tissues, organs and the catheter 62 through which it is inserted. Furthermore, a blunted tip reduces the potential for scraping of the interior of the catheter wall which can create undesirable shavings which can migrate into the patient's body cavity. The interior lumen 33 of the inner cannula 15 terminates at a distal opening 38 and proximal opening 35 and functions as a conduit for transporting fluids and/or air. The distal portion 32 of the inner cannula 15 contains at least one lateral opening 18 located proximally to the distal tip 34 of the inner cannula 15 and distally from the distal end 21 of the outer cannula 14 when the inner cannula 15 is in the fully extended position relative to the outer cannula 14.

The number, size, shape and positioning of lateral openings 18 on the inner cannula 15 can vary. When the inner cannula 15 is residing within the outer cannula 14 and is in the fully extended position, and distal tip 32 of the inner cannula 15 protrudes beyond the distal end 21 of the outer cannula 14 and the lateral opening(s) 18 on the inner cannula 15 is/are exposed and unobstructed by the outer cannula 14. Accordingly, when an aspiration device is proximally coupled to the cannula assembly 10 and aspiration is effected, fluid is permitted to flow into the inner cannula 15 through the lateral opening(s) 18 and through the internal lumen 33 exiting out the proximal end 31 of the inner cannula 15.

Referring to FIGS. 3 and 4, the inner cannula 15 and outer cannula 14 are constructed so as to permit the inner cannula 15 to move relative to the outer cannula 14 when the cannula assembly 10 is in the unlocked position. The cannula assembly housing 11 contains a biasing element 40 which biases the inner cannula 15 toward its fully extended position whereby the distal tip 34 extends beyond the distal end 21 of the outer cannula 14. The proximal end 31 of the inner cannula 15 further comprises an adaptor 41 coupled thereto for reversible connection to an aspiration device. The inner cannula adaptor 41 can be in the form of any suitable conduit-forming reversible coupling construction, such as a threaded or luer connection. When an aspiration device (not shown) is coupled to the adaptor 41 at the proximal end 42 of the cannula assembly 10 portion of the device, a closed circuit is created between the distal lateral opening 38 of the inner cannula 15 and the aspiration device, the entire length of the interior lumen 33 of the inner cannula serving as a contiguous conduit.

The cannula assembly housing 11 is constructed so as to contain a mechanism for permitting movement of the inner cannula relative to the outer cannula, and a mechanism means for removably coupling the cannula assembly 10 to the valve assembly 30. The mechanism for permitting movement between the inner and outer cannulas can be any structure whereby the available longitudinal motion between the inner and outer cannulas is physically restricted, but the movement within such available motion is not. In one embodiment, the proximal portion 31 of the inner cannula 15 can comprise an inner cannula hub 50 attached thereto, and the proximal portion of the outer cannula 14 can comprise an outer cannula hub 51 attached thereto. The cannula assembly housing 11 by way of its construct contains, and provides the physical barrier for, the maximum extension of the inner cannula hub 50 relative to the outer cannula hub 51. The cannula assembly housing 11 also contains a biasing element 40 which biases the inner cannula 15 towards its fully extended position. The biasing element 40 can be any resilient structure which can exert a reversible force sufficient to fully extend the inner cannula. In the figures, the biasing element is depicted as a spring contained within the cannula assembly housing 11 and interacts with the inner cannula hub 50 and therefore the corresponding inner cannula The availability of movement between the inner cannula and outer cannula is coordinated by a locking mechanism activated upon disengagement of the cannula assembly 10 from the valve assembly 30.

Figure 6:
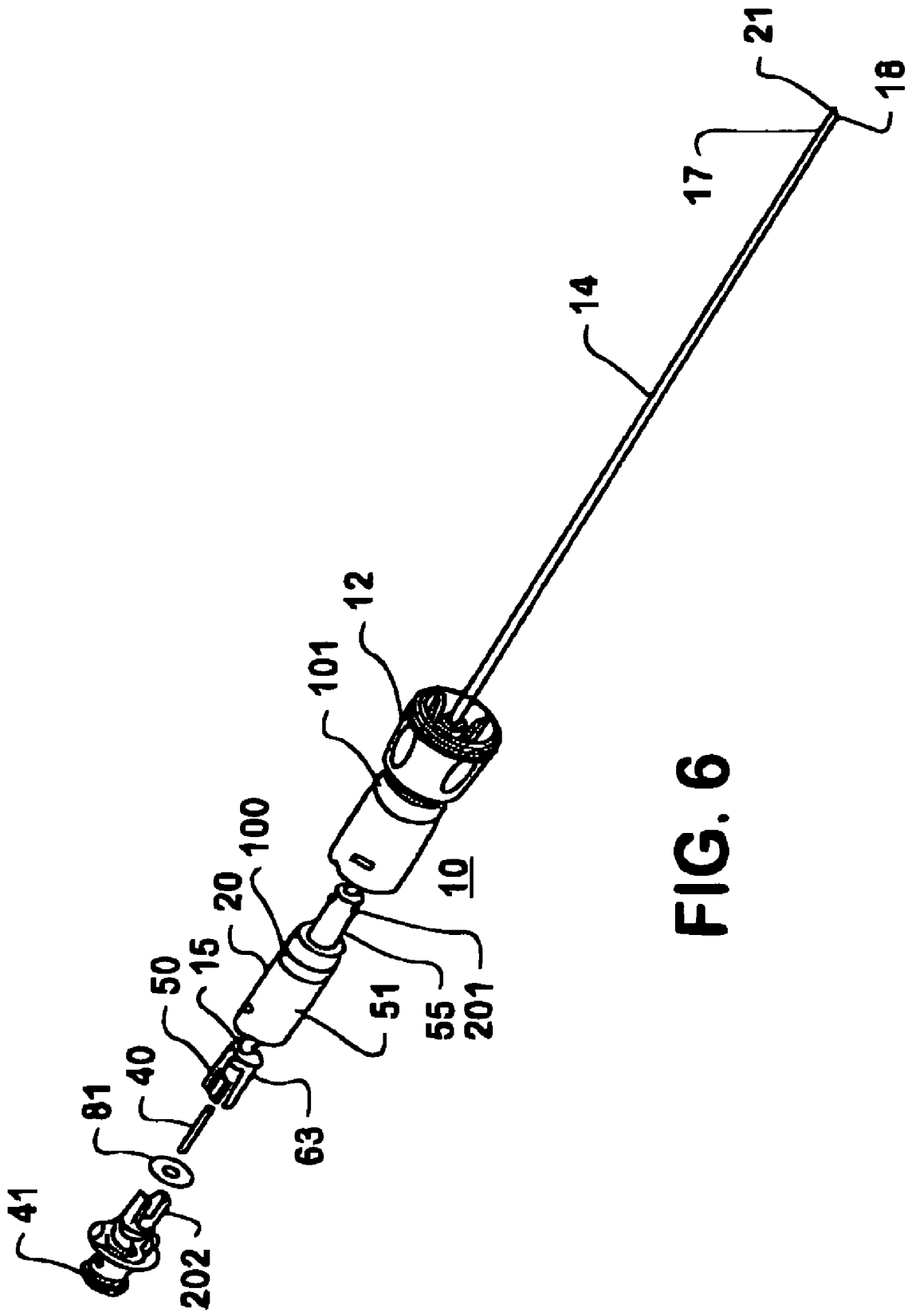
FIG. 6 is an exploded perspective view of the cannula assembly portion of the device showing individual components according to one embodiment of the invention.
Figure 7:
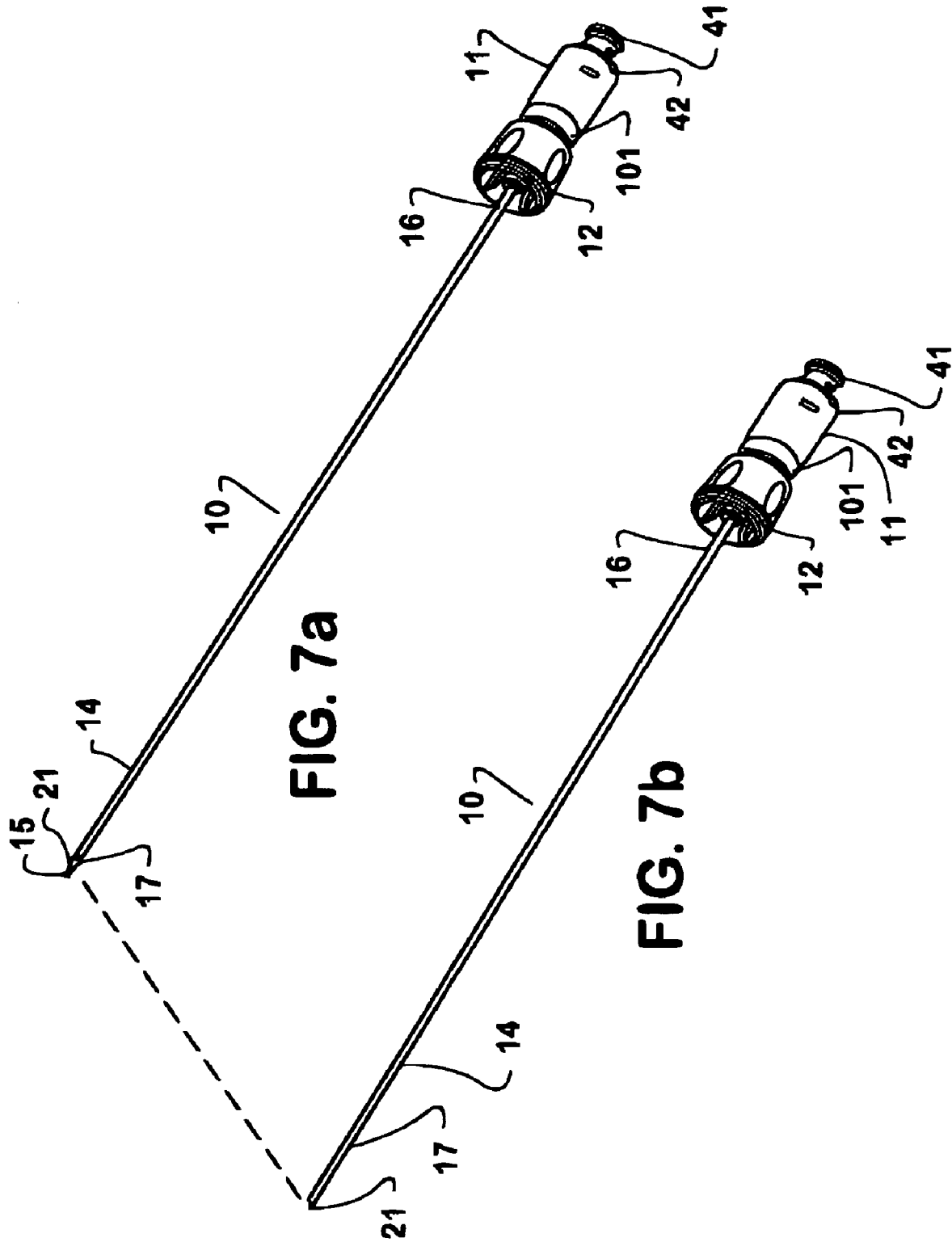
FIGS. 7A and 7B together illustrate the movement of the inner and outer cannulas and the corresponding change of the externally viewable indicator.

Referring to FIGS. 6, 7A and 7B, the cannula assembly housing also contains an externally viewable indicator which reveals the positioning of the inner cannula relative to the outer cannula. A variety of externally viewable indicator structures can be used provided they produce a visible change which corresponds to the movement of the inner cannula relative to the outer cannula.

In one embodiment and as illustrated in detail in FIG. 6, the externally viewable indicator is in the form of a colorized band 63 on the inner cannula hub 50, which is apparent or concealed relative to an opening 100 through the outer cannula hub 51 and a transparent portion 101 of the cannula assembly housing 11. Now referring to FIGS. 7A and 7B, the movement of the inner cannula 15 in a proximal direction causes the appearance, or alternatively concealment of, the color band 63 on the inner cannula hub 50 through the outer cannula hub opening 100 and cannula assembly housing transparent portion 101 to the user. In FIGS. 7A and 7B, the cannula assembly is depicted without the valve assembly attached for clarity of illustration purposes, and it will be understood that the ability for the inner cannula to move relative to the outer cannula is dependent upon the attachment and detachment of the cannula assembly to the valve assembly in accordance with the invention. During a procedure, the indicator informs the practitioner that the distal tip of the assembled device, i.e., the cannula assembly and catheter assembly, has encountered a solid or semi-solid surface without the need for endoscopic viewing techniques. A variety of different indicator designs and configurations can be used in accordance with the invention, provided they produce a readily apparent change in appearance. A variety of colors, symbols, or other indicia arrangements can be used.

The device of the invention can further comprise a locking mechanism controlled by the coupling of the cannula assembly 10 and the valve assembly 30. According to one embodiment, the coupling of the cannula assembly and valve assembly automatically deactivates the locking mechanism so as to permit movement of the inner cannula 15 relative to the outer cannula 14. The locking mechanism can be constructed comprising two interacting structures which control the activation and deactivation of the lock.

In one embodiment and as illustrated in the FIGS. 3 and 4, one component of the locking mechanism comprises rotational alignment groove(s) 200 located within the interior wall of the proximal portion 79 of the valve assembly 30. The rotational alignment groove(s) 200 engage protrusion(s) 201 located on the exterior surface at the distal portion 55 of the outer cannula hub 51. The fitting of the cannula assembly 10 into the proximal portion 79 of the valve assembly 30 therefore controls the rotational orientation of the outer cannula hub 51 and the inner cannula hub 50 residing therein while the outermost handled housing of the cannula assembly 10 and valve assembly 30 are simply fitted in the longitudinal direction. The rotational orientation of the inner cannula hub 50 relative to a peg 202 located at the proximal interior portion of the cannula assembly housing 11 either permits or prevents proximal longitudinal movement of the inner cannula hub 50 and inner cannula 15. The peg 202 is configured to cooperate with the configuration of the inner cannula hub 50 in a manner which either permits the proximal portion of the inner cannula hub 50 to fit or slide proximally into the peg 202, or when the inner cannula hub 50 is rotated slightly prevents the inner cannula hub 50 from further movement in the proximal direction. The peg 202 can integrally molded onto a portion of the cannula assembly housing 11. In practice, therefore, just as the engagement of the cannula assembly 10 to the valve assembly 30 deactivates the locking mechanism and allows the inner cannula 15 to move relative to the outer cannula 14, disengagement of the cannula assembly 10 from the valve assembly 30 activates the locking mechanism and prevents the inner cannula 15 from moving. In addition to securing the cannula components of the device, the locking mechanism provides an automatic safety device with the detachment and removal of the cannula assembly which avoids or reduces the likelihood of accidental puncture of tissue by the sharp distal end 21 of the outer cannula 15 during handling of the cannula assembly.

The cannula assembly housing 11 can further contain a gasket 81 located between the inner cannula hub 50 and outer cannula hub 51 in the housing so as to create a fluid tight seal or environmental barrier between inner cannula 15 and outer cannula 14 within the housing. In one embodiment, the gasket 81 is shown in the figures as an "o-ring" valve.

Figure 2:
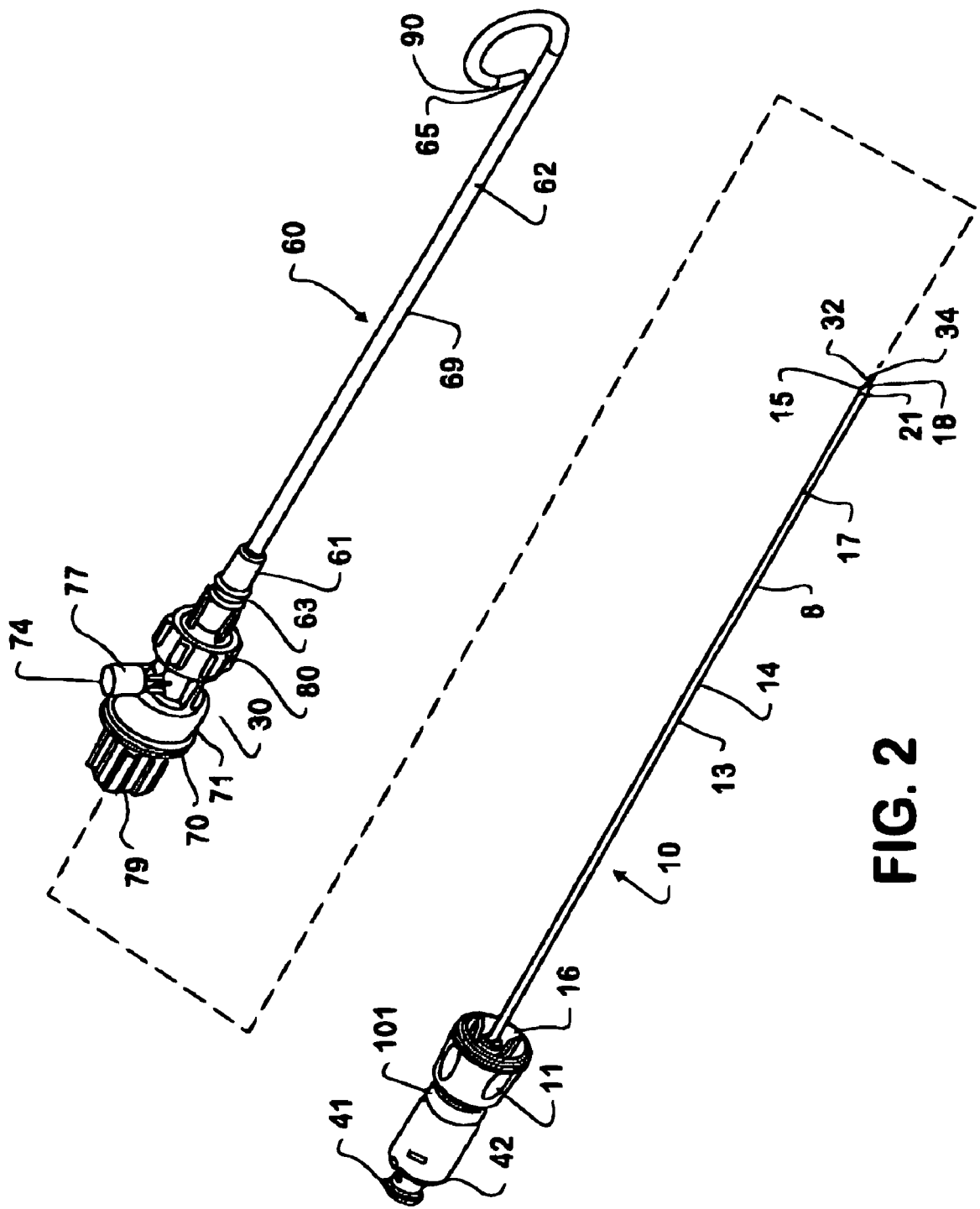
FIG. 2 is a side view of the cannula assembly separated and shown alongside the coupled valve assembly and catheter assembly in accordance with one embodiment of the invention.

The distal portion 12 of the cannula assembly housing 11 is removably attached or engaged to the proximal end 79 of the valve assembly 30 as depicted in FIG. 2. The corresponding interacting components of each of the cannula assembly housing 11 and valve assembly 30 are constructed for removable attachment from one another.

Referring again to FIGS. 3 and 4, the valve assembly 30 generally comprises a valve housing 71 having a proximal end 79 and a distal end 80, interior chamber 72, reinsertible valve 73 positioned within said chamber, and a lateral access port 74 in communication with the interior chamber 72. The valve assembly 30 contains a proximal opening 75 and distal opening 76 in communication with the interior chamber 72. The valve assembly 30 is constructed to permit removable engagement of both the cannula assembly 10 and catheter assembly 60 thereto. As shown in FIG. 4, when attached, the cannula assembly 10 is positioned such that the cannula assembly housing 11 attaches to the proximal portion 79 of the valve assembly 30, and the inner cannula 15 and outer cannula 14 superimposed thereon, are inserted through the valve assembly 30 penetrating the reinsertible valve 73 and residing within the interior chamber 72, and exiting the valve assembly at the distal end 80 residing within the catheter assembly 60.

The reinsertible valve 73 of the valve assembly 30 can be any structure adapted to repeatedly accommodate a cannula structure and continuously maintain a seal circumscribing the cannula when inserted therethrough. The reinsertible valve 73 can be composed of any resilient or elastic material, such as rubber. A variety of reinsertible valve structures are possible, provided insertion, removal and reinsertion of the cannula can be performed. Examples of reinsertible valve structures include, but are not limited to, a slit valve, and a centrally perforated diaphragm.

The lateral access port 74 is located distally to the reinsertible valve 73. The lateral access port 74 contains a conduit in communication with the interior chamber 72 of the valve assembly, and adaptor 77 for attachment of additional tubing, valves, and the like, forming a conduit in communication with the interior chamber 72 of the valve assembly 30. The positioning of the reinsertible valve 73 proximally to the lateral access port 74 continually maintains a fluid/air tight barrier and closed circuit both during and after the removal of the cannula assembly from the valve assembly 30 and catheter assembly 60. This continuous maintenance of the closed circuit is important for preventing the migration of air and fluid into and out of the valve assembly and, accordingly, the external and internal environments are not co-mingled. The device of the invention, therefore, can continuously maintain a closed system throughout the use of the device provided the valve assembly is present. This closed system can be maintained during insertion and removal of the cannula assembly, as well as during fluid withdrawal through the lateral access port. Furthermore, the closed system can be maintained even with the reinsertion and reattachment of the cannula assembly portion of the device.

Figure 8:
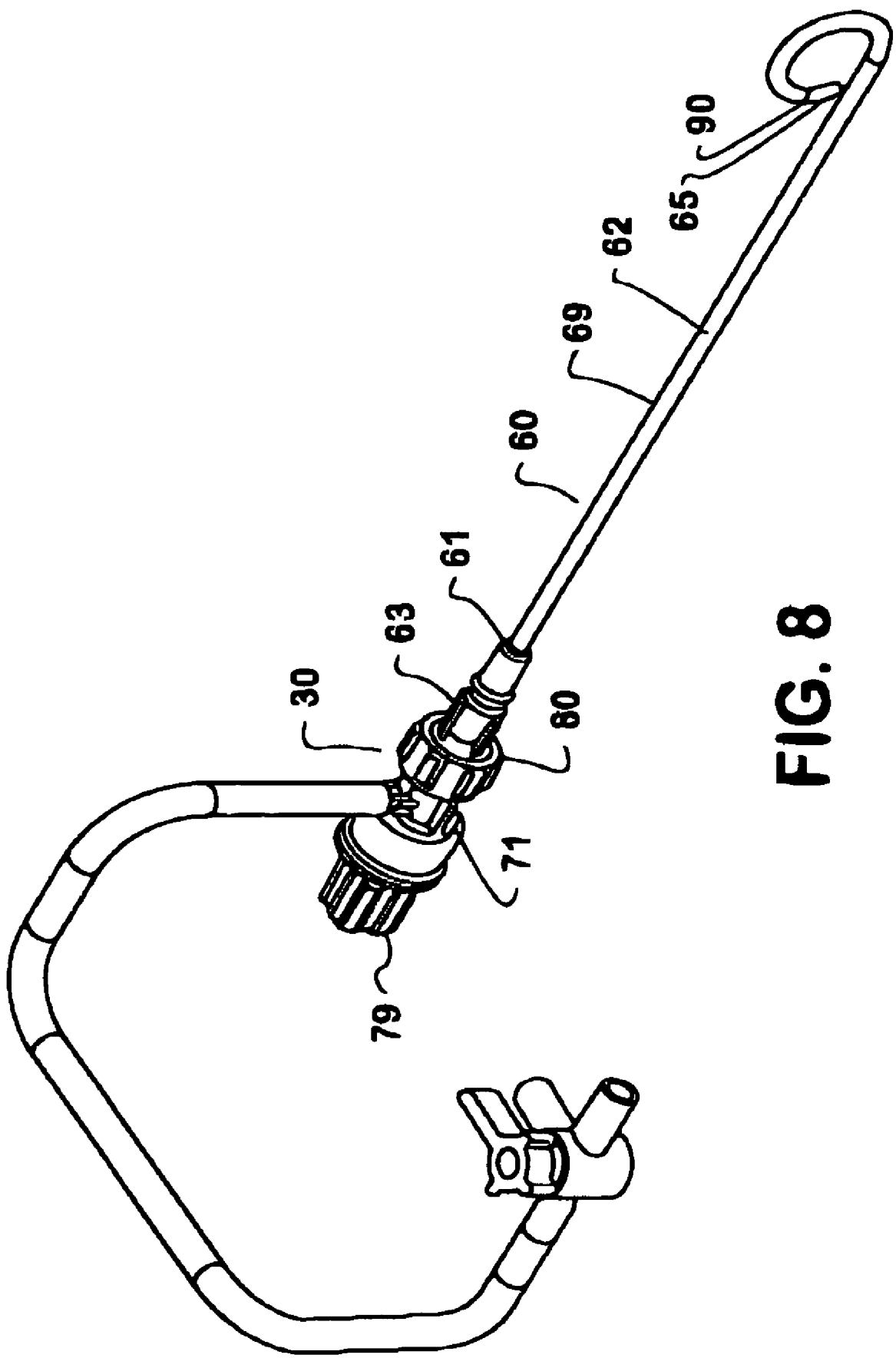
FIG. 8 is an overall perspective view of the valve assembly component of the device according to one embodiment of the invention showing additional attachments to the lateral access port.
Figure 9:
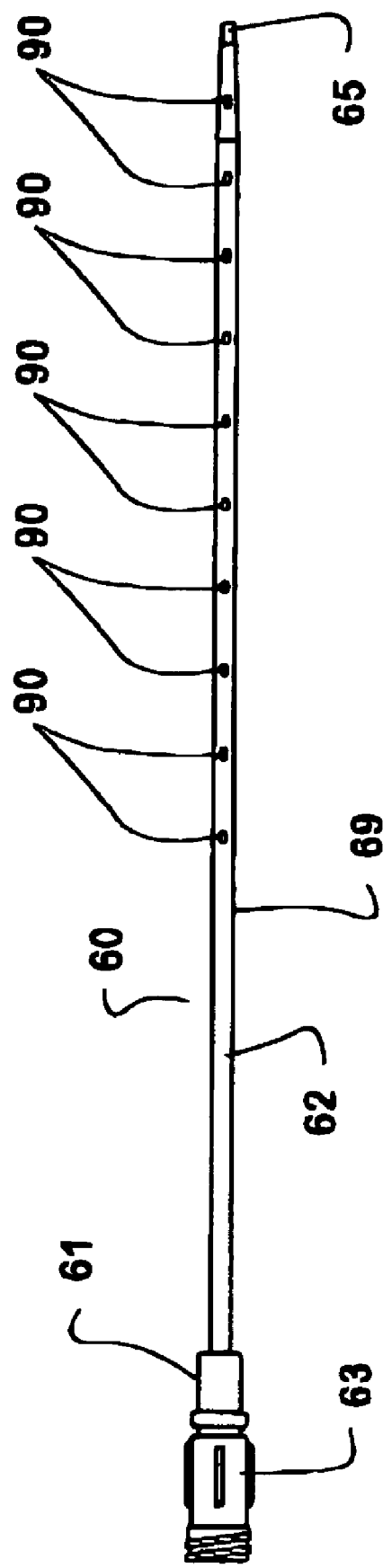
FIG. 9 is an overall perspective view of the catheter assembly component of the device in accordance with one embodiment of the invention.

Referring now to FIGS. 8 and 9, the catheter assembly 60 comprises a flexible catheter 62 having a proximal end 61 and distal end 65 and coupled to a catheter hub 63 and is adapted to accommodate the inner and outer cannulas inserted therethrough. The distal ends of both the inner and outer cannulas when assembled extend further beyond the distal end 65 of the catheter 62 as shown in FIG. 1. The catheter hub 63 is coupled to the catheter 62 body at the proximal end 61 and comprises an adaptor for removably coupling the catheter assembly 60 to the distal end of the valve assembly while maintaining a conduit in communication with both components. One example of a suitable adaptor is a threaded or luer assembly.

Upon detachment of the cannula assembly 10 and withdrawal of the inner and outer cannulas from within the lumen of the catheter 62, the catheter can be used to passively or actively. An aspiration device can be attached to the lateral access port 74 of the valve assembly 30, to actively transport fluid from the patient's body cavity to the external environment as shown in FIG. 8. In a further embodiment, the adaptor on the catheter hub 63 can be constructed to interchangeably attach to both the valve assembly 30 and an additional aspiration device directly, for example. Accordingly, the valve assembly can be disengaged from the catheter assembly 60 thereby providing the option of aspiring fluid directly from the catheter without the valve assembly 30.

Figure 10:
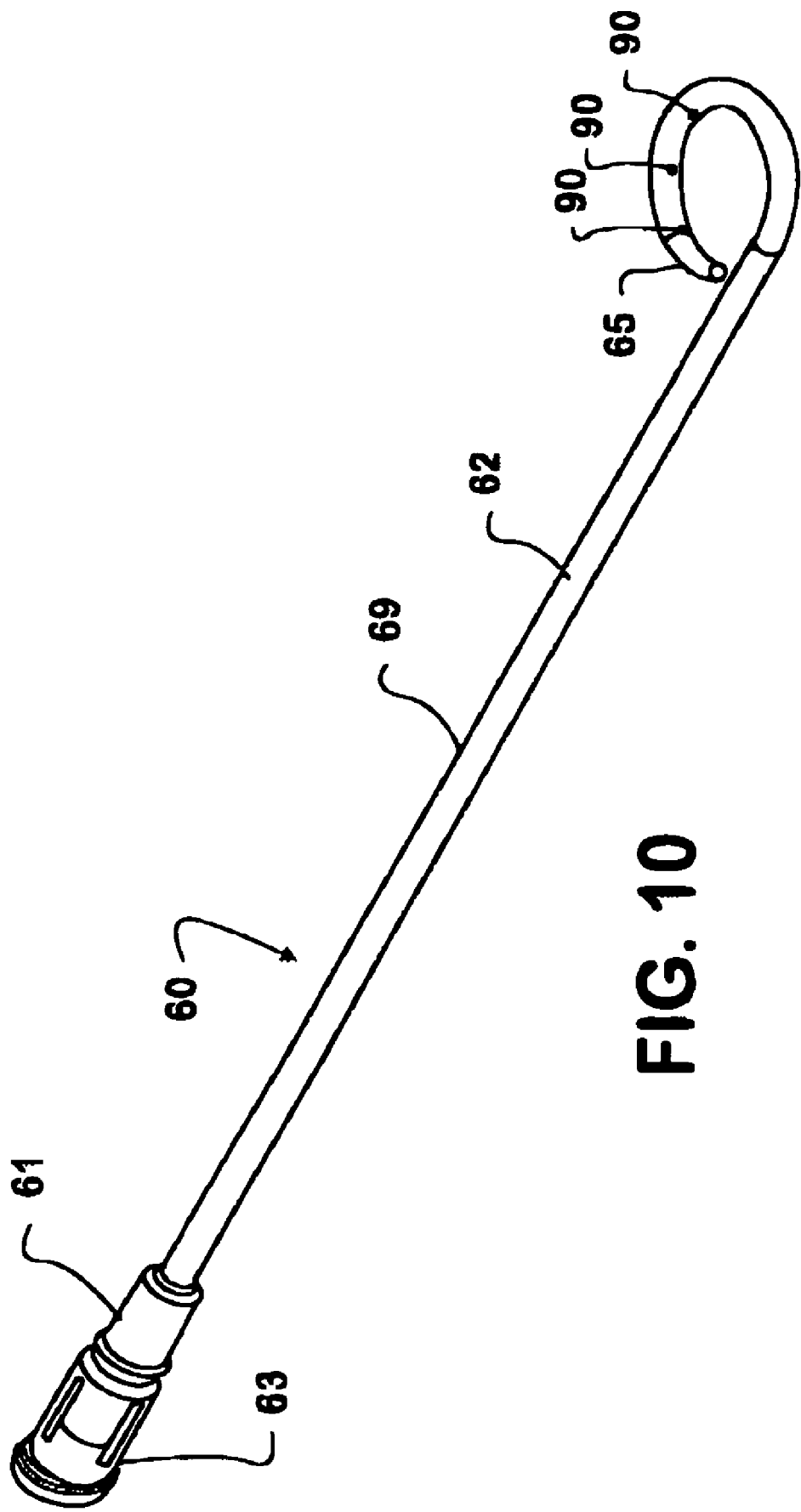
FIG. 10 is an angled side view perspective of the catheter assembly component of the device showing a coiled configuration and alignment of external openings in accordance with one embodiment of the invention.

Referring to FIGS. 9 and 10, the flexible catheter 62 comprises a catheter body 69, an internal lumen longitudinally running therethrough (not shown), and at least one opening 90 in communication with said lumen. The number, size, shape and spacing of opening(s) 90 can vary. The flexible catheter body 69 can be composed of any suitable material typically used for insertible catheters, such as silicone and polyurethane. In a further embodiment, the surface of the catheter body can be treated with a lubricity enhancing substance or biomaterial to facilitate insertion and positioning of catheter within the patient and its movement within the body.

In a preferred embodiment, the flexible catheter 62 comprises a predetermined resting-state configuration which is different from the substantially linear configuration when the cannula assembly 10 is placed therein. One embodiment of a predetermined resting state configuration is illustrated in FIGS. 2, 8 and 10. In other words, the inner and outer cannulas can function as a "stylet" during insertion and positioning of the catheter within the patient's body. Once the cannulas are removed from within the catheter 62, the catheter returns to its original resting-state configuration. "Predetermined resting-state configuration" is intended to describe the overall configuration that the catheter is biased toward by virtue of its manufactured configuration without influence by additional structures, such as the cannulas when placed therein.

A variety of pre-determined resting-state configurations can be used for the catheter 62. Suitable predetermined configurations include, but are not limited to, substantially linear, serpentine, curved and coiled configurations. Preferably, the configuration is one which when positioned within the intended body site, cooperates with the surrounding anatomy to perform its function. In one embodiment and as illustrated in FIGS. 8 and 10, the flexible catheter 62 has a predetermined resting-state configuration of a single coil, sometimes referred to as a "pig tail" configuration.

In a preferred embodiment, the number, size, shape and positioning of the openings 90 of the catheter 62 are coordinated with the pre-determined resting-state configuration and arranged and oriented to minimize the likelihood of obstruction of the openings when placed adjacent to surrounding anatomy within the site. One such configuration and opening arrangement is illustrated in FIG. 10, which shows a single coil wherein the openings are arranged in a substantially linear pattern along the interior of the coil such that when the coil is placed against a planar surface, the openings are raised off of the surface. Accordingly, fluid ingress through the catheter openings and into the catheter lumen is facilitated.

The paracentesis device of the invention permits at least three manners in which to conduct an aspiration procedure. In a first arrangement, aspiration can be conducted through the proximal end of the completely assembled device by coupling of an aspiration device to the cannula assembly and drawing fluid through the inner cannula. Aspiration can also be conducted by coupling an aspiration device directly or indirectly to the lateral access port of the valve assembly with the cannula assembly completely removed from the catheter. As a third alternative, an aspiration device can be directly coupled onto the catheter hub with both the valve assembly and cannula assembly removed. The device of the invention, therefore, offers the practitioner a variety of aspiration alternatives by virtue of its structures and interactions between the components.

The plastic components of the device can be composed of conventional polymeric materials suitable for use in the medical device field. The metallic components of the device can be composed of any metal or metallic alloy composition suitable for use in medical devices. Preferably, the materials used for the device are sterilizable. The components of the device, whether plastic or metallic, and the assembly of the entire device, can be accomplished using readily available and conventional equipment and techniques. Examples of typical techniques include injection molding, metal molding, grinding and polishing techniques, and the like.

The device of the invention can be provided to the user in the form of a kit accompanied by additional surgical instruments and equipment. Examples of additional surgical instruments and equipment include, but are not limited to, syringes, scalpels, bandages, suturing materials, tubing, prepping materials, and the like.

The following example is intended to illustrate the use of one embodiment of the invention and is not intended to be construed as limiting the claims.

EXAMPLE

Thoracentesis Procedure Using the Device of the Invention

A general outline of a thoracentesis procedure using one embodiment of the device of the invention is as follows:

The patient is prepped for surgery in accordance with standard medical protocol for a thoracentesis procedure. The device of the invention is removed from its packaging and the components are assembled. The some or all of the components of the device are presented to the practitioner in assembled condition. Additional attachments or equipment can also be pre-assembled on the device. For example, tubing can be pre-coupled to the lateral access port of the valve assembly to eliminate the need for the practitioner to do so later during the procedure. Likewise, the aspiration device to be used can be attached to the proximal end of the device of the invention prior to inserting the device into the patient's body. It will be recognized that the order of assembly and attachment of additional components onto the device of the invention can vary according to the practitioner's preference and patient's needs.

If not pre-assembled, the cannula assembly is inserted through the valve assembly and further inserted into the catheter assembly. The longitudinal insertion of the cannula assembly within the catheter functions to straighten the catheter into a linear configuration from the predetermined resting state configuration thereof. The rounded distal tip of the inner cannula extending beyond the distal end of the outer cannula of the cannula assembly functions to reduce or avoid unintentional penetration or puncture of the catheter wall during the insertion of the cannula assembly into and through the interior lumen of the catheter. Furthermore, the blunted tip of the inner cannula cooperates with the predetermined resting state configuration of the catheter so as to gradually ease the curvature of the catheter into a straightened linear configuration. A third advantage of the rounded tip of the inner cannula is that it reduces the likelihood of scraping the interior surface of the catheter body and creating undesirable foreign particulate matter which can migrate into the patient's body.

The insertion and coupling of the cannula assembly to the valve assembly converts the cannula assembly from locked to unlocked position once the hub portions of each assembly meet thereby permitting the inner cannula to move freely relative to the outer cannula. Once the cannula assembly is secured onto the valve assembly and catheter assembly, the distal portion of the device can be inserted into the patient's body and in proximity to the desired thoracentesis site. The position of the inner cannula relative to the outer cannula can be continuously monitored by the practitioner throughout the duration of the procedure by viewing the externally viewable indicator. The indicator assembly can be constructed so as to cause a change in color corresponding to differences in the inner cannula movement thereby alerting the practitioner to the change. Both the motion of the inner cannula within the outer cannula and the corresponding activation of the indicator are resilient such that the full distal extension of the inner cannula readily returns upon avoidance of the obstacle and this event is immediately viewable by way of the indicator. During insertion and positioning within the patient's body, if the distal tip of the inner cannula encounters solid or semi-solid tissue, the force of tissue exerted on the inner cannula tip causes the inner cannula to move and simultaneously alters the indicator to revealing this condition to the practitioner. Accordingly, no endoscopic viewing is needed in order for the nature of tissue or cavity space encountered to be ascertained during the steering of the device within the body.

Once the desired position in the pleural cavity is reached, the practitioner can then attach and/or actuate the aspiration device to withdraw the fluid from the patient's body. While the cannula assembly is attached to the valve and catheter assemblies, the fluid is drawn into and through the distal opening(s) located at the distal portion of the inner cannula. The fluid flows through the interior lumen of the inner cannula and into the aspiration device or its associated components, e.g., the reservoir within a syringe. The practitioner may wish to periodically attempt to withdrawn fluid during the insertion and positioning of the device since accomplishing the withdrawal of fluid can be used to confirm that the desired location within the body has been reached or, alternatively, obtain a series of fluid samples for diagnostic procedures if desired.

Once the use of the cannula assembly is completed for the time being, the practitioner can disengage the cannula assembly from the valve assembly and remove the cannula assembly from the catheter assembly and valve assembly. Just as insertion of the cannula assembly straightened the catheter configuration, the removal of the cannula assembly permits the flexible catheter to return to its predetermined resting state configuration. The disengagement of the cannula assembly from the valve assembly automatically returns the cannula assembly to its locked position thereby restricting the longitudinal axial movement of the inner cannula relative to the outer cannula. The locked position of the cannula assembly such that the rounded tip of the inner cannula is extended beyond the distal tip of the outer cannula provides a blunt end so as to reduce the likelihood of accidental puncture during the handling of the cannula assembly apart from the remaining components of the device. In the locked position, the cannula assembly is once again available for re-insertion through the valve assembly and the catheter assembly.

Although the catheter can have a variety of pre-determined resting-state configurations, preferably the function of the catheter in fluid withdrawal is optimized by utilizing a pre-determined configuration which minimizes the risk of occlusion of the openings in the catheter. In the case of the coiled "pigtail" configuration, wherein the tendency of the catheter when positioned in a cavity adjacent to tissue or organs will be for the planar orientation to align with the plane of the adjacent tissue, the openings on the catheter are preferably oriented toward the center of the coil avoiding contact and occlusion by surrounding tissue and permitting free unobstructed ingress of fluid therethrough. Another advantage of a looped or coiled catheter configuration is that it discourages encroachment of surrounding tissues toward the region within the coil.

In addition to the change in configuration of the catheter, removing the cannula assembly portion of the device also causes the valve to close thereby creating a closed fluid circuit between the catheter, the distal side of the valve in the valve assembly, and the lateral access port and associated tubing attached thereto, the circuit being impervious to environmental fluid or air. Associated tubing can comprise a valve or other control means to manipulate movement of fluid within the closed circuit. The lateral access side port and associated tubing and valves can then be used to further aspire or permit passive drainage of fluid from the catheter placement site in the body. If employed, aspiration can be accomplished using any suitable and readily available aspiration device or system, including but not limited to, syringes, bulbs, vacuum sources, and the like.

Optionally, if a closed fluid circuit system utilizing the valve assembly is not needed or desired, the valve assembly can be detached from the catheter assembly and tubing or other equipment can be coupled directly to the catheter hub of the catheter assembly for fluid removal.

Once the desired fluid has been removed from the patient, the catheter and valve assemblies can be withdrawn from the patients body, and the wound can be closed. Alternatively, if occlusion has been encountered or repositioning of the catheter is otherwise desired, the cannula assembly can be reinserted and the procedure can be repeated.

INDUSTRIAL APPLICABILITY

The device of the invention is useful in paracentesis procedures such as thoracentesis wherein greater precision and flexibility of usage is desired in the operation of the device while maintaining the attributes desired for successful performance of the invasive procedure, e.g., maintenance of separate external and internal environments throughout the procedure. The device of the invention offers the practitioner greater precision and safety in the handling of the device. The device affords the practitioner a variety of aspiration alternatives thereby permitting operation of the device in accordance with a particular patient's needs. All of these features provide a device that is an advancement in the art.

The invention has been described with reference to various specific and preferred embodiments and techniques. It will be understood, however, that reasonable variations and modification of such embodiments and techniques are possible while remaining within the spirit and scope of the invention.

What is claimed is:

1. A device for use in paracentesis comprising:
   a) a cannula assembly comprising an inner cannula having an internal lumen and at least one lateral opening located proximal to its distal end, an outer cannula adapted to accommodate said inner cannula within, and cannula assembly housing, said inner cannula being movable relative to said outer cannula;
   b) a valve assembly comprising a valve housing, interior chamber, reinsertible valve positioned within said chamber, and a lateral access port, said valve assembly adapted to removably attach to said cannula assembly and to accommodate a portion of said cannula assembly when placed within;
   c) a catheter assembly comprising a flexible catheter having an internal lumen and at least one opening, said catheter assembly adapted to removably attach to said valve assembly and to accommodate the distal portion of said cannula assembly placed within;
   wherein said cannula assembly further comprises a locking mechanism controlled by a coupling of said cannula assembly to said valve assembly; and
   wherein said locking mechanism permits movement of the inner cannula relative to the outer cannula when the cannula assembly is engaged to said valve assembly, and which restricts the movement of said inner cannula relative to said outer cannula upon disengagement of the cannula assembly from said valve assembly.

2. A device for use in paracentesis comprising:
   a) cannula assembly comprising an inner cannula having an internal lumen and at least one lateral opening located proximal to its distal end, an outer cannula adapted to accommodate said inner cannula within, and cannula assembly housing, said inner cannula being movable relative to said outer cannula;
   b) a valve assembly; and
   c) a locking mechanism controlled by a coupling of said cannula assembly to said valve assembly, wherein said locking mechanism permits movement of the inner cannula relative to the outer cannula when the cannula assembly is engaged to said valve assembly, and which restricts a movement of said inner cannula relative to said outer cannula upon disengagement of the cannula assembly from said valve assembly.

3. A device comprising:
   a cannula assembly comprising an inner cannula having an internal lumen and at least one lateral opening located proximal to its distal end, an outer cannula adapted to accommodate said inner cannula within, and cannula assembly housing, said inner cannula being movable relative to said outer cannula;
   a catheter assembly comprising a flexible catheter having an internal lumen and adapted to removably accommodate the distal portion of said cannula assembly placed within;
   a locking mechanism permitting movement of said inner cannula relative to the outer cannula when the cannula assembly is engaged and which restricts a movement of said inner cannula relative to said outer cannula upon disengagement of the cannula assembly.

* * * * *